United States Patent
Ai et al.

(10) Patent No.: US 12,233,098 B2
(45) Date of Patent: Feb. 25, 2025

(54) **PREPARATION METHOD OF *ANTRODIA CINNAMOMEA* WATER-INSOLUBLE DIETARY FIBER**

(71) Applicant: UNIVERSITY OF SHANGHAI FOR SCIENCE AND TECHNOLOGY, Shanghai (CN)

(72) Inventors: Lianzhong Ai, Shanghai (CN); Yongjun Xia, Shanghai (CN); Peng Meng, Shanghai (CN); Hui Zhang, Shanghai (CN); Guangqiang Wang, Shanghai (CN); Zhiqiang Xiong, Shanghai (CN); Xin Song, Shanghai (CN)

(73) Assignee: UNIVERSITY OF SHANGHAI FOR SCIENCE AND TECHNOLOGY, Shanghai (CN)

( * ) Notice: Subject to any disclaimer, the term of this patent is extended or adjusted under 35 U.S.C. 154(b) by 753 days.

(21) Appl. No.: 17/431,145

(22) PCT Filed: Sep. 11, 2020

(86) PCT No.: PCT/CN2020/114638
§ 371 (c)(1),
(2) Date: Aug. 13, 2021

(87) PCT Pub. No.: WO2021/174801
PCT Pub. Date: Sep. 10, 2021

(65) Prior Publication Data
US 2022/0305069 A1     Sep. 29, 2022

(30) Foreign Application Priority Data
Mar. 2, 2020   (CN) .............. 202010135376

(51) Int. Cl.
*A61K 36/07*   (2006.01)
*A23L 31/00*   (2016.01)
*A23L 33/21*   (2016.01)
*A61P 3/06*    (2006.01)
*B01D 11/02*   (2006.01)

(52) U.S. Cl.
CPC .............. *A61K 36/07* (2013.01); *A23L 31/00* (2016.08); *A23L 33/21* (2016.08); *A61P 3/06* (2018.01); *B01D 11/0288* (2013.01); *A23V 2002/00* (2013.01); *A61K 2236/331* (2013.01); *A61K 2236/333* (2013.01); *A61K 2236/39* (2013.01); *A61K 2236/51* (2013.01)

(58) Field of Classification Search
None
See application file for complete search history.

(56) References Cited

PUBLICATIONS

Yuan (CN 109467613—English translation), Mar. 15, 2019.*

* cited by examiner

*Primary Examiner* — Susan Hoffman
(74) *Attorney, Agent, or Firm* — H&I PARTNERS; Chai Im; C. Andrew Im

(57) ABSTRACT

A preparation method of *Antrodia cinnamomea* water-insoluble dietary fiber. After ethanol and water extraction, *Antrodia cinnamomea* wastes are dried and superfine-comminuted to obtain *Antrodia cinnamomea* waste powder. The waste powder treated with NaOH solution containing NaBH4 is extracted it twice to obtain two extracts. The two extracts are combined and an appropriate amount of glacial acetic acid are added for neutralization. The extracts are centrifugalized and precipitate is collected. After washing the precipitate with ultrapure water, the precipitate is dissolved with LiCl-DMSO. The precipitate that is insoluble in the LiCl-DMSO solution is dialyzed and freeze-dried to obtain the water-insoluble dietary fiber component ACA-IDK of *Antrodia cinnamomea*. The LiCl-DMSO solution is subjected to ethanol/DMSO fractional precipitation, and then the precipitate is collected and dialyzed. The water-insoluble dietary fiber component ACA-DK of *Antrodia cinnamomea* is obtained after freeze-drying.

7 Claims, 1 Drawing Sheet

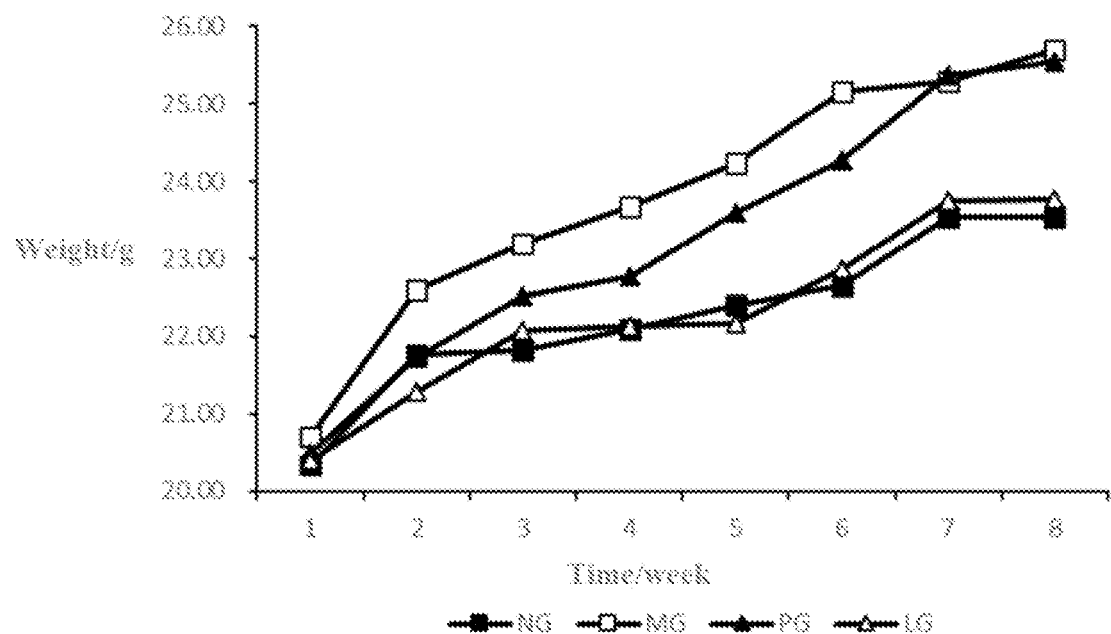

PREPARATION METHOD OF ANTRODIA CINNAMOMEA WATER-INSOLUBLE DIETARY FIBER

RELATED APPLICATIONS

This application is a § 371 application of PCT/CN2020/114638 filed Sep. 11, 2020, which claims priority from Chinese Patent Application No. 202010135376.9 filed Mar. 2, 2020, each of which is incorporated herein by reference in its entirety.

FIELD OF THE INVENTION

The present invention relates to the technical field of industrial waste reuse, in particular to a method for preparing water-insoluble dietary fiber of *Antrodia cinnamomea*.

BACKGROUND OF THE INVENTION

Dietary fiber is a general term that refers to ingredients in plant based food, carbohydrates and their analogs that are not digested and absorbed in the human small intestine but can be fully or partially fermented by microorganisms in the large intestine. It is known as the seventh nutrient. Dietary fibers have strong adsorption characteristics, including water-holding, oil-holding, water-absorbing, swelling and appearing gelatinous, as well as the adsorption of heavy metals. According to its solubility, dietary fibers can be divided into water-insoluble dietary fiber and water-soluble dietary fiber. Among them, water-insoluble dietary fiber can stimulate intestinal peristalsis, soften and accelerate bowel movements, reduce the re-collection of harmful substances in feces, and have a good preventive and auxiliary treatment effect on obesity, constipation, hyperlipidemia and other diseases. It is an ideal functional food ingredients. Water-insoluble dietary fibers are mainly plant cell wall components, including cellulose, hemicellulose, lignin and chitosan. Studies show that insufficient dietary fiber intake can lead to a variety of health problems such as sugar and lipid metabolism disorders, and cardiovascular diseases.

*Antrodia cinnamomea*, also known as *Antrodia camphorata* or niu-chang-chih, has the reputation of "forest ruby" in Taiwan. *Antrodia cinnamomea* contains many active ingredients, including triterpenoids, polysaccharides, ubiquinones, superoxide dismutase, ergosterol, etc. It has physiological activities such as anti-tumor, immunity enhancement and anti-bacteria. *Antrodia cinnamomea* polysaccharide has good anti-tumor and immunity enhancement activity. At present, most researches mainly focus on the fermentation, extraction and function evaluation of water-soluble polysaccharides. In the industrial production, after the fruit body or mycelium of *Antrodia cinnamomea* is extracted with ethanol and water, the alcohol-soluble compounds and water-soluble polysaccharides are basically extracted. However, the residue still contains a large amount of water-insoluble dietary fiber. The present invention provides a method for preparing water-insoluble dietary fiber of *Antrodia cinnamomea*. The prepared dietary fiber has high extraction purity, is suitable for large-scale production, and can effectively reduce the lipid metabolism disorder caused by a high-fat diet.

SUMMARY OF THE INVENTION

To solve the above technical problems, the present invention provides a preparation method of *Antrodia cinnamomea* water-insoluble dietary fiber.

The present invention provides a preparation method of *Antrodia cinnamomea* water-insoluble dietary fiber, characterized by that comprising steps as follow:

Step (1): after ethanol and water extraction, the *Antrodia cinnamomea* wastes are dried and superfine-comminuted to obtain *Antrodia cinnamomea* waste powder;

Step (2): treat the *Antrodia cinnamomea* waste powder with NaOH solution containing NaBH4, extract it twice to obtain two extracts with a material-to-liquid ratio of 1:5-1:25 v/m;

Step (3): combine the two extracts and add an appropriate amount of glacial acetic acid for neutralization, after the first predetermined time, centrifugalize the extracts and collect the precipitate;

Step (4): after washing the precipitate 3 times with ultrapure water, dissolve the precipitate with LiCl-DMSO, the precipitate that is insoluble in the LiCl-DMSO solution is dialyzed for the second predetermined time and freeze-dried to obtain the water-insoluble dietary fiber component ACA-IDK of *Antrodia cinnamomea*; and Step (5): the LiCl-DMSO solution is subjected to ethanol/DMSO fractional precipitation, and the ethanol addition ratio is 30%%-90% v/v, and then the precipitate is collected and dialyzed for the third predetermined time, the water-insoluble dietary fiber component ACA-DK of *Antrodia cinnamomea* is obtained after freeze-drying.

Further, the preparation method of *Antrodia cinnamomea* water-insoluble dietary fiber is characterized by that: wherein the *Antrodia cinnamomea* wastes in step (1) include fruiting bodies of *Antrodia cinnamomea*, *Antrodia cinnamomea* dish-cultured thallus, *Antrodia cinnamomea* grain solid-state fermentation thallus and *Antrodia cinnamomea* liquid-state fermentation mycelium.

Further, the preparation method of *Antrodia cinnamomea* water-insoluble dietary fiber is characterized by that: wherein the concentration of the NaOH solution in step (2) is 0.1-1.0 mol/L, and the content of NaBH4 is 0.1 M.

Further, the preparation method of *Antrodia cinnamomea* water-insoluble dietary fiber is characterized by that: wherein the extraction temperature in step (2) is 2-15° C., extraction time is 4 h-24 h.

Further, the preparation method of *Antrodia cinnamomea* water-insoluble dietary fiber is characterized by that: wherein the first predetermined time in step (3) is 2 h.

Further, the preparation method of *Antrodia cinnamomea* water-insoluble dietary fiber is characterized by that: wherein the second predetermined time in step (4) is 3 days, the concentration of LiCl in LiCl-DMSO solution is 0.25 mol/L.

Further, the preparation method of *Antrodia cinnamomea* water-insoluble dietary fiber is characterized by that: wherein the third predetermined time in step (5) is 3 days.

The present invention also provides an application of the preparation method of the *Antrodia cinnamomea* water-insoluble dietary fiber in food additives and meal replacement foods, wherein the application is for reducing cholesterol and fat.

According to the method for preparing water-insoluble dietary fiber of *Antrodia cinnamomea* in the present invention, the process is simple and suitable for large-scale production. The prepared water-insoluble dietary fiber has high extraction rate and high purity. It is suitable for large-scale production, and is a high-quality water-insoluble diet fiber that can effectively absorb oil and cholesterol. In addition, water-insoluble dietary fiber can effectively alleviate the lipid metabolism disorder caused by high-fat diet. And it has the effect of lowering cholesterol and lipids, thereby reducing weight. Also, the method effectively uses the wastes after extraction of *Antrodia cinnamomea*, with low cost, good economy benefits and good prospect development.

BRIEF DESCRIPTION OF THE DRAWINGS

FIG. 1 is the effect of *Antrodia cinnamomea* insoluble dietary fiber on the body weight of mice in the embodiment of the present invention.

DETAILED DESCRIPTION OF THE INVENTION

The present invention is further described in detail below with reference to specific embodiments and FIGURES for a better understanding of the technical means and effects. The following embodiments are preferred cases of the present invention. And the present invention is not only limited to these embodiments.

The present invention provides a preparation method of *Antrodia cinnamomea* water-insoluble dietary fiber, characterized by that comprising steps as follow:

Step (1): after ethanol and water extraction, the *Antrodia cinnamomea* wastes are dried and superfine-comminuted to obtain *Antrodia cinnamomea* waste powder;

Step (2): treat the *Antrodia cinnamomea* waste powder with NaOH solution containing NaBH4, extract it twice to obtain two extracts with a material-to-liquid ratio of 1:5-1:25 v/m;

Step (3): combine the two extracts and add an appropriate amount of glacial acetic acid for neutralization, after the first predetermined time, centrifugalize the extracts and collect the precipitate;

Step (4): after washing the precipitate 3 times with ultrapure water, dissolve the precipitate with LiCl-DMSO, the precipitate that is insoluble in the LiCl-DMSO solution is dialyzed for the second predetermined time and freeze-dried to obtain the water-insoluble dietary fiber component ACA-IDK of *Antrodia cinnamomea*; and Step (5): the LiCl-DMSO solution is subjected to ethanol/DMSO fractional precipitation, and the ethanol addition ratio is 30%%-90% v/v, and then the precipitate is collected and dialyzed for the third predetermined time, the water-insoluble dietary fiber component ACA-DK of *Antrodia cinnamomea* is obtained after freeze-drying.

Further, the preparation method of *Antrodia cinnamomea* water-insoluble dietary fiber is characterized by that: wherein the *Antrodia cinnamomea* wastes in step (1) include fruiting bodies of *Antrodia cinnamomea*, *Antrodia cinnamomea* dish-cultured thallus, *Antrodia cinnamomea* grain solid-state fermentation thallus and *Antrodia cinnamomea* liquid-state fermentation mycelium.

Further, the preparation method of *Antrodia cinnamomea* water-insoluble dietary fiber is characterized by that: wherein the concentration of the NaOH solution in step (2) is 0.1-1.0 mol/L, and the content of NaBH4 is 0.1 M.

Further, the preparation method of *Antrodia cinnamomea* water-insoluble dietary fiber is characterized by that: wherein the extraction temperature in step (2) is 2-15° C., extraction time is 4 h-24 h.

Further, the preparation method of *Antrodia cinnamomea* water-insoluble dietary fiber is characterized by that: wherein the first predetermined time in step (3) is 2 h.

Further, the preparation method of *Antrodia cinnamomea* water-insoluble dietary fiber is characterized by that: wherein the second predetermined time in step (4) is 3 days, the concentration of LiCl in LiCl-DMSO solution is 0.25 mol/L.

Further, the preparation method of *Antrodia cinnamomea* water-insoluble dietary fiber is characterized by that: wherein the third predetermined time in step (5) is 3 days.

The present invention also provides an application of the preparation method of the *Antrodia cinnamomea* water-insoluble dietary fiber in food additives and meal replacement foods, wherein the application is for reducing cholesterol and fat.

In the present invention, food additives with the effects of lowering cholesterol and lipid levels can be used in foods such as bread, biscuits, dairy products, meat products, beverages, etc. Meal replacement foods with the effects of lowering cholesterol and lipid levels can be prepared into powders, granules, tablets, capsules, etc.

The experimental methods used in the following embodiments are conventional methods unless otherwise specified; the materials and reagents used can be obtained from commercial sources unless otherwise specified.

Embodiment 1

Step (1): after ethanol and water extraction, the *Antrodia cinnamomea* wastes are dried and superfine-comminuted to obtain *Antrodia cinnamomea* waste powder.

Step (2): treat the *Antrodia cinnamomea* waste powder with NaOH solution with a concentration of 0.1 mol/L and containing 0.01 M NaBH4, extract it twice to obtain two extracts with a material-to-liquid ratio of 1:5 v/m. The extraction temperate is 2° C. and the extraction time is 4 h.

Step (3): combine two said extracts and add an appropriate amount of glacial acetic acid for neutralization, after 2 h, centrifugalize the said extracts and collect the precipitate.

Step (4): after washing the precipitate 3 times with ultrapure water, dissolve the precipitate with LiCl-DMSO with a LiCl concentration of 0.25 mol/L, the precipitate that is insoluble in the LiCl-DMSO solution is dialyzed for the 3 days and freeze-dried to obtain the water-insoluble dietary fiber component ACA-IDK of *Antrodia cinnamomea*.

Step (5): said LiCl-DMSO solution is subjected to ethanol/DMSO fractional precipitation, and the ethanol addition ratio is 30% v/v, and then the precipitate is collected and dialyzed for 3 days, the water-insoluble dietary fiber component ACA-DK of *Antrodia cinnamomea* is obtained after freeze-drying.

The extraction rate of the insoluble dietary fiber component ACA-DK in this embodiment was 3.6%, and the purity was 68.5%; the extraction rate of ACA-IDK was 4.6%, and the purity was 63.4%.

Embodiment 2

Step (1): after ethanol and water extraction, the *Antrodia cinnamomea* wastes are dried and superfine-comminuted to obtain *Antrodia cinnamomea* waste powder.

Step (2): treat the *Antrodia cinnamomea* waste powder with NaOH solution with a concentration of 0.6 mol/L and containing 0.01 M NaBH4, extract it twice to obtain two extracts with a material-to-liquid ratio of 1:10 v/m. The extraction temperate is 10° C. and the extraction time is 12 h.

Step (3): combine two said extracts and add an appropriate amount of glacial acetic acid for neutralization, after 2 h, centrifugalize the said extracts and collect the precipitate.

Step (4): after washing the precipitate 3 times with ultrapure water, dissolve the precipitate with LiCl-DMSO with a LiCl concentration of 0.25 mol/L, the precipitate that is insoluble in the LiCl-DMSO solution is dialyzed for the 3 days and freeze-dried to obtain the water-insoluble dietary fiber component ACA-IDK of *Antrodia cinnamomea*.

Step (5): said LiCl-DMSO solution is subjected to ethanol/DMSO fractional precipitation, and the ethanol addition ratio is 70% v/v, and then the precipitate is collected and dialyzed for 3 days, the water-insoluble dietary fiber component ACA-DK of *Antrodia cinnamomea* is obtained after freeze-drying.

The extraction rate of the insoluble dietary fiber component ACA-DK in this embodiment was 8.7%, and the purity was 88.3%; the extraction rate of ACA-IDK was 9.2%, and the purity was 82.7%.

Embodiment 3

Step (1): after ethanol and water extraction, the *Antrodia cinnamomea* wastes are dried and superfine-comminuted to obtain *Antrodia cinnamomea* waste powder.

Step (2): treat the *Antrodia cinnamomea* waste powder with NaOH solution with a concentration of 1.0 mol/L and containing 0.01 M NaBH4, extract it twice to obtain two extracts with a material-to-liquid ratio of 1:25 v/m. The extraction temperate is 20° C. and the extraction time is 24 h.

Step (3): combine two said extracts and add an appropriate amount of glacial acetic acid for neutralization, after 2 h, centrifugalize the said extracts and collect the precipitate.

Step (4): after washing the precipitate 3 times with ultrapure water, dissolve the precipitate with LiCl-DMSO with a LiCl concentration of 0.25 mol/L, the precipitate that is insoluble in the LiCl-DMSO solution is dialyzed for the 3 days and freeze-dried to obtain the water-insoluble dietary fiber component ACA-IDK of *Antrodia cinnamomea*.

Step (5): said LiCl-DMSO solution is subjected to ethanol/DMSO fractional precipitation, and the ethanol addition ratio is 90% v/v, and then the precipitate is collected and dialyzed for 3 days, the water-insoluble dietary fiber component ACA-DK of *Antrodia cinnamomea* is obtained after freeze-drying.

The extraction rate of the insoluble dietary fiber component ACA-DK in this embodiment was 8.8%, and the purity was 77.3%; the extraction rate of ACA-IDK was 9.1%, and the purity was 70.8%.

Embodiment 4

Step (1): after ethanol and water extraction, the *Antrodia cinnamomea* wastes are dried and superfine-comminuted to obtain *Antrodia cinnamomea* waste powder.

Step (2): treat the *Antrodia cinnamomea* waste powder with NaOH solution with a concentration of 0.6 mol/L and containing 0.01 M NaBH4, extract it twice to obtain two extracts with a material-to-liquid ratio of 1:10 v/m. The extraction temperate is 10° C. and the extraction time is 12 h.

Step (3): combine two said extracts and add an appropriate amount of glacial acetic acid for neutralization, after 2 h, centrifugalize the said extracts and collect the precipitate.

Step (4): after washing the precipitate 3 times with ultrapure water, dissolve the precipitate with LiCl-DMSO with a LiCl concentration of 0.25 mol/L, the precipitate that is insoluble in the LiCl-DMSO solution is dialyzed for the 3 days and freeze-dried to obtain the water-insoluble dietary fiber component ACA-IDK of *Antrodia cinnamomea*.

Step (5): said LiCl-DMSO solution is subjected to ethanol/DMSO fractional precipitation, and the ethanol addition ratio is 70% v/v, and then the precipitate is collected and dialyzed for 3 days, the water-insoluble dietary fiber component ACA-DK of *Antrodia cinnamomea* is obtained after freeze-drying.

The extraction rate of the insoluble dietary fiber component ACA-DK in this embodiment was 8.3%, and the purity was 89.1%; the extraction rate of ACA-IDK was 8.8%, and the purity was 84.2%.

Embodiment 5

Step (1): after ethanol and water extraction, the *Antrodia cinnamomea* wastes are dried and superfine-comminuted to obtain *Antrodia cinnamomea* waste powder.

Step (2): treat the *Antrodia cinnamomea* waste powder with NaOH solution with a concentration of 0.6 mol/L and containing 0.01 M NaBH4, extract it twice to obtain two extracts with a material-to-liquid ratio of 1:10 v/m. The extraction temperate is 10° C. and the extraction time is 12 h.

Step (3): combine two said extracts and add an appropriate amount of glacial acetic acid for neutralization, after 2 h, centrifugalize the said extracts and collect the precipitate.

Step (4): after washing the precipitate 3 times with ultrapure water, dissolve the precipitate with LiCl-DMSO with a LiCl concentration of 0.25 mol/L, the precipitate that is insoluble in the LiCl-DMSO solution is dialyzed for the 3 days and freeze-dried to obtain the water-insoluble dietary fiber component ACA-IDK of *Antrodia cinnamomea*.

Step (5): said LiCl-DMSO solution is subjected to ethanol/DMSO fractional precipitation, and the ethanol addition ratio is 70% v/v, and then the precipitate is collected and dialyzed for 3 days, the water-insoluble dietary fiber component ACA-DK of *Antrodia cinnamomea* is obtained after freeze-drying.

The extraction rate of the insoluble dietary fiber component ACA-DK in this embodiment was 7.7%, and the purity was 86.4%; the extraction rate of ACA-IDK was 8.3%, and the purity was 83.3%.

The following tests were carried out on the water-insoluble dietary fiber component ACA-DK of *Antrodia cinnamomea* in Embodiments 1-5:

Lipid-Lowering Function Test (Animal Test)

1. Test Conditions

Samples: The water-insoluble dietary fiber component ACA-DK of *Antrodia cinnamomea*, which is prepared as a suspension of a certain concentration and placed at 4° C. for further use.

Test animals: 40 C57BL/6 SPF-grade mice weighing 18-22 g were purchased from Shanghai JieSijie Experimental Animal Co., Ltd. (license No. SCXK20180004). They were randomly divided into 4 groups with 10 mice in each group.

Main instruments and reagents: Balance, centrifuge, Illumina MiSeq sequencer, microplate reader, RNA extraction kit.

Test method: In test environment, the mice were divided into the following 4 groups: Normal group NG (gavage with normal saline), model group MG (high-fat diet), positive control group PG (gavage with lovastatin) and insoluble dietary fiber group LG. Mice in normal group NG were fed with basic feed, and mice in the rest of the groups were fed with high-fat feed. For mice in insoluble dietary fiber group LG, gavage with the dietary fiber was administered once a day for 8 weeks.

Feeding conditions: Mice were raised in an IVC system with a temperature of 18-22° C. and a relative humidity of 40-70%. License No. of the laboratory animal using license is SCXK20180004. The irradiated sterile feed for mice was purchased from Jiangsu Synergy Pharmaceutical Bioengineering Co., Ltd.

Basic feed: Flour 20%, bran 25%, corn 20%, rice flour 10%, soybean meal 20%, fish meal 2%, bone meal 2%, salt 0.9%, vitamin 0.1%;

High-fat feed: Lard 10%, sucrose 5%, cholesterol 1%, bile salt 0.3%, basic feed 83.7%.

Data Analysis:

SPSS 22.0 software was used to statistically analyze the original data of each experiment, and the ANOVA program was used to test the significance of the data.

2. Test Result Analysis (1) Effect of *Antrodia cinnamomea* Insoluble Dietary Fiber on Body Weight of Mice.

FIG. 1 is the effect of *Antrodia cinnamomea* insoluble dietary fiber on the body weight of mice in the embodiment of the present invention.

As shown in FIG. 1, compared with mice in the normal group, the mice fed with high-fat diet for 8 weeks gained weight significantly, with a weight gain rate of 24.15%. While for the mice fed with *Antrodia cinnamomea* insoluble dietary fiber for 8 weeks, there was no significant difference in body weight compared with mice in the normal group. The weight gain rate was only 16.54%. So *Antrodia cinnamomea* insoluble dietary fiber can reduce weight.

(2) Effects of *Antrodia cinnamomea* Insoluble Dietary Fiber on Serum Lipids in Mice.

As shown in Table 1, compared with the mice in the normal group, after 8 weeks of feeding on a high-fat diet, LDL-C of these mice increased significantly, up to 10.33±1.91 mmol/L, while HDL-C decreased slightly. And after 8 weeks of oral administration of *Antrodia cinnamomea* insoluble dietary fiber, LDL-C of these mice decreased significantly, which is only 2.43±0.28 mmol/L. The risk factor of atherosclerosis (LDL-C/HDL-C) decreased from 4.83 in the MG group to 1.38 in the LG group. So the insoluble dietary fiber of *Antrodia cinnamomea* can regulate the metabolism of serum lipoprotein.

TABLE 1

Effects of *Antrodia cinnamomea* insoluble dietary fiber on serum lipids in mice

| Group | HDL-C (mmol/L) | LDL-C (mmol/L) |
|---|---|---|
| NG | 2.89 ± 0.44 $^{BC}$ | 1.86 ± 0.61 $^{a}$ |
| MG | 2.14 ± 0.40 $^{CD}$ | 10.33 ± 1.91 $^{c}$ |
| PG | 2.45 ± 0.20 $^{D}$ | 7.73 ± 3.07 $^{b}$ |
| LG | 1.76 ± 0.56 $^{AB}$ | 2.43 ± 0.28 $^{a}$ |

(3) Effects of *Antrodia cinnamomea* Insoluble Dietary Fiber on TG and TC in Mice.

As shown in Table 2, compared with the mice in the normal group, after 8 weeks of feeding on a high-fat diet, total cholesterol (TC) of these mice was increased significantly, up to 0.075±0.019 mmol/g protein. While triglycerides (TG) showed no significant difference. After 8 weeks of oral administration of *Antrodia cinnamomea* insoluble dietary fiber, the content of TC and TG of these mice both decreased significantly, which were 0.023±0.007 and 0.042±0.015 mmol/g protein, respectively. So *Antrodia cinnamomea* insoluble dietary fiber has the effect of reducing TC and TG.

TABLE 2

Effects of *Antrodia cinnamomea* insoluble dietary fiber on TG and TC in mice

| Group | TG(mmol/g prot) | TC(mmol/g prot) |
|---|---|---|
| NG | 0.080 ± 0.021 $^{A}$ | 0.027 ± 0.010 $^{a}$ |
| MG | 0.083 ± 0.024 $^{A}$ | 0.075 ± 0.019 $^{b}$ |
| PG | 0.031 ± 0.019 $^{B}$ | 0.024 ± 0.005 $^{a}$ |
| LG | 0.042 ± 0.015 $^{B}$ | 0.023 ± 0.007 $^{a}$ |

According to Embodiment 1-3, when *Antrodia cinnamomea* fruiting bodies are used as raw materials, the concentration of NaOH solution is 0.6 mol/L, the extraction temperature is 10° C., and the extraction time is 12 hours, the extraction rate and purity of the insoluble dietary fiber component ACA-DK are higher.

According to embodiments 4 and 5, under the same conditions as in Embodiment 2, when the raw materials are *Antrodia cinnamomea* dish-cultured cells and *Antrodia cinnamomea* liquid fermentation mycelium, the extraction rate and purity of the insoluble dietary fiber components ACA-DK and ACA-IDK are higher.

According to the animal test, further research has been done on the water-insoluble dietary fiber component of *Antrodia cinnamomea* ACA-DK, and the prepared water-insoluble dietary fiber of *Antrodia cinnamomea* has good water-holding, oil-holding and cholesterol absorption properties, and can effectively alleviate the lipid metabolism disorder caused by high-fat diet. It can reduce the increase in blood lipids and cholesterol in mice caused by a high-fat diet. And it can control or reduce weight.

In summary, according to the method for preparing water-insoluble dietary fiber of *Antrodia cinnamomea* in the present invention, the process is simple and suitable for large-scale production. The prepared water-insoluble dietary fiber has high extraction rate and high purity. It is suitable for large-scale production, and is a high-quality water-insoluble diet fiber that can effectively absorb oil and cholesterol. In addition, water-insoluble dietary fiber can effectively alleviate the lipid metabolism disorder caused by high-fat diet. And it has the effect of lowering cholesterol and lipids, thereby reducing weight. Also, the method effectively uses the wastes after extraction of *Antrodia cinnamomea*, with low cost, good economy benefits and good prospect development.

The invention claimed is:

1. A preparation method of *Antrodia cinnamomea* water-insoluble dietary fiber, comprising:

extracting ethanol and water from a fruit body or mycelium of *Antrodia cinnamomea* to obtain *Antrodia cinnamomea* wastes, which are residues remaining after the ethanol and water extraction, the *Antrodia cinnamomea* wastes are dried and comminuted to obtain an *Antrodia cinnamomea* waste powder;

treating the *Antrodia cinnamomea* waste powder with an NaOH solution containing NaBH$_4$ and extracting twice therefrom to obtain two extracts with a material-to-liquid ratio of 1:5-1:25 v/m;

combining the two extracts and adding a glacial acetic acid for neutralization, after a first predetermined time, centrifugalizing the extracts to collect a precipitate;

washing the precipitate three times with water and dissolving the precipitate in a LiCl-DMSO solution, the precipitate that is insoluble in the LiCl-DMSO solution is dialyzed for a second predetermined time and freeze-dried to obtain a water-insoluble dietary fiber component of *Antrodia cinnamomea* that is insoluble in DMSO referred to as ACA-IDK; and subjecting the LiCl-DMSO solution to an ethanol/DMSO fractional precipitation, an ethanol addition ratio being 30%-90% v/v, then collecting the precipitate, dialyzing the precipitate for a third predetermined time, and freeze-drying the precipitate to obtain the water-insoluble dietary fiber component of *Antrodia cinnamomea* that is soluble in DMSO referred to as ACA-DK.

2. The preparation method of *Antrodia cinnamomea* water-insoluble dietary fiber of claim 1, wherein the *Antrodia cinnamomea* wastes comprise fruiting bodies of *Antrodia cinnamomea*, *Antrodia cinnamomea* dish-cultured thallus, *Antrodia cinnamomea* grain solid-state fermentation thallus and *Antrodia cinnamomea* liquid-state fermentation mycelium.

3. The preparation method of *Antrodia cinnamomea* water-insoluble dietary fiber of claim 1, wherein a concentration of the NaOH solution is 0.1-1.0 mol/L and a content of $NaBH_4$ is 0.1 M.

4. The preparation method of *Antrodia cinnamomea* water-insoluble dietary fiber of claim 1, wherein the step of extracting twice from the treated *Antrodia cinnamomea* waste powder is at an extraction temperature of 2-15° C. and for an extraction time of 4-24 hours.

5. The preparation method of *Antrodia cinnamomea* water-insoluble dietary fiber of claim 1, wherein the first predetermined time is 2 hours.

6. The preparation method of *Antrodia cinnamomea* water-insoluble dietary fiber of claim 1, wherein the second predetermined time is 3 days and a concentration of LiCl in the LiCl-DMSO solution is 0.25 mol/L.

7. The preparation method of *Antrodia cinnamomea* water-insoluble dietary fiber of claim 1, wherein the third predetermined time is 3 days.

* * * * *